(12) United States Patent
Ichikawa

(10) Patent No.: US 8,927,781 B2
(45) Date of Patent: Jan. 6, 2015

(54) METHOD FOR PRODUCING ETHANOL

(75) Inventor: Masaru Ichikawa, Tokyo (JP)

(73) Assignees: Ichikawa Office Inc., Tokyo (JP); Mitsui Engineering & Shipbuilding Co. Ltd., Tokyo (JP)

( * ) Notice: Subject to any disclaimer, the term of this patent is extended or adjusted under 35 U.S.C. 154(b) by 361 days.

(21) Appl. No.: 13/148,398

(22) PCT Filed: Feb. 12, 2010

(86) PCT No.: PCT/JP2010/000861
§ 371 (c)(1),
(2), (4) Date: Dec. 7, 2011

(87) PCT Pub. No.: WO2010/092819
PCT Pub. Date: Aug. 19, 2010

(65) Prior Publication Data
US 2012/0071697 A1    Mar. 22, 2012

(30) Foreign Application Priority Data
Feb. 12, 2009  (JP) ................. 2009-054173

(51) Int. Cl.
C07C 27/04 (2006.01)
C10J 3/00 (2006.01)
B01J 23/58 (2006.01)
B01J 23/656 (2006.01)
B01J 23/80 (2006.01)
B01J 23/89 (2006.01)
B01J 37/02 (2006.01)
C07C 29/151 (2006.01)
B01J 21/08 (2006.01)
C10J 3/48 (2006.01)

(52) U.S. Cl.
CPC .. *C10J 3/00* (2013.01); *B01J 23/58* (2013.01); *B01J 23/6562* (2013.01); *B01J 23/80* (2013.01); *B01J 23/8926* (2013.01); *B01J 23/8993* (2013.01); *B01J 37/0207* (2013.01); *C07C 29/1518* (2013.01); *B01J 21/08* (2013.01); *C10J 2300/0916* (2013.01); *C10J 2300/092* (2013.01); *C10J 2300/0973* (2013.01); *C10J 2300/1665* (2013.01); *C10J 2300/1853* (2013.01); *Y02E 50/18* (2013.01); *Y02E 50/32* (2013.01); *C10J 3/48* (2013.01); *C10J 2300/0976* (2013.01); *C10J 2300/0986* (2013.01)
USPC ............ 568/885; 568/840; 518/700; 502/113

(58) Field of Classification Search
CPC ....... B01J 2523/00; C10G 2/32; C07C 33/02; C07C 29/149
USPC .................... 568/840, 885; 518/700; 502/113
See application file for complete search history.

(56) References Cited

U.S. PATENT DOCUMENTS 6,346,555 B1 *  2/2002  Luo et al. ...................... 518/713

FOREIGN PATENT DOCUMENTS

JP            61178935 A  *  8/1986
WO    WO 2007117590 A2  *  10/2007

* cited by examiner

*Primary Examiner* — Sudhakar Katakam
(74) *Attorney, Agent, or Firm* — Law Offices of Peter H. Priest, PLLC

(57) ABSTRACT

A method for producing ethanol by which ethanol can be synthesized from less fermentable biomass materials such as plant-derived materials and rice straws and industrial waste biomass materials such as wooden building materials and pulp and which can therefore broaden the range of raw materials for the production of ethanol. Specifically, a method for producing ethanol including reacting a raw material gas obtained by a thermochemical gasification reaction of biomass in the presence of a catalyst containing rhodium, at least one transition metal, and at least one element selected from lithium, magnesium and zinc.

4 Claims, 1 Drawing Sheet

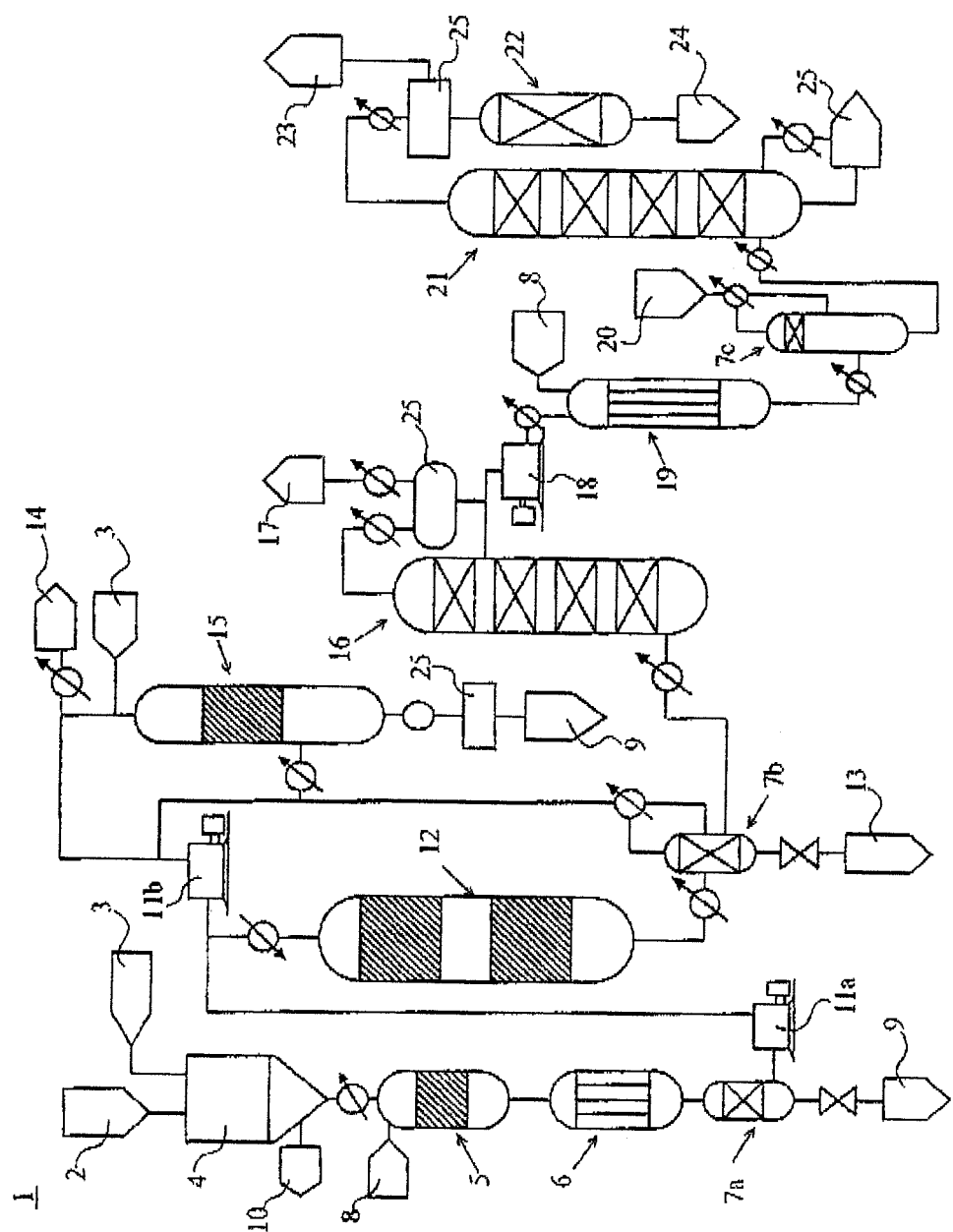

METHOD FOR PRODUCING ETHANOL

TECHNICAL FIELD

The present invention relates to a method for producing ethanol, and, more particularly, to a method for producing ethanol using a raw material gas generated by a thermochemical gasification reaction of biomass, in other words, renewable biological organic resources except fossil resources.

BACKGROUND ART

As part of measures against global warming, measures to reduce emission of carbon dioxide, which is believed to be a major contributor to global warming, are demanded. As biomass grows by photosynthetic fixation of carbon dioxide, it has various proposed applications as a major candidate which does not increase carbon dioxide emission.

Above all, establishment of an effective method for producing ethanol, which is an important chemical expected to serve as an automotive fuel, from biomass is desired.

As a method for producing ethanol from biomass, a method for synthesis of ethanol directly from biomass using a biological process such as fermentation has been proposed.

However, the pretreatment to convert lignin and cellulose contained in woody biomass in an amount of approximately 30% by mass into ethanol has technical and economical problems because it requires a number of steps and a high cost. Another problem is that the rate of utilization of biomass is so low that a large amount of biomass residue is generated.

On the other hand, methods for the production of a gas composed primarily of hydrogen, carbon monoxide, lower hydrocarbons such as methane and ethane, and carbon dioxide from biomass by thermochemical gasification have been proposed (refer to Patent Document 1, for example). In the following, a gas generated by thermochemical gasification of biomass is referred to as "biomass gas."

In a thermochemical gasification reaction of biomass, a gasification furnace having a fixed bed or fluidized bed is usually used to generate a gas mixture of carbon monoxide and hydrogen. However, the problem is that the gas mixture contains such a small proportion of hydrogen depending on the generation conditions that it is not suitable as a raw material for efficient synthesis of ethanol when used for direct synthesis of ethanol.

RELATED ART DOCUMENT

Patent Document

Patent Document 1: Published Japanese Translation of PCT Application No 2009-532483

SUMMARY OF THE INVENTION

Problem to be Solved by the Invention

The object of the present invention is to provide a method for producing ethanol by which a raw material gas containing hydrogen and carbon monoxide which is obtained by gasification of biomass can be directly converted into ethanol with high efficiency and high yield.

Means for Solving the Problem

The present invention provides method for producing ethanol, including reacting a raw material gas obtained by a thermochemical gasification reaction of biomass in the presence of a catalyst containing rhodium, at least one transition metal, and at least one element selected from lithium, magnesium and zinc.

Also provided is the method for producing ethanol, in which the catalyst is any one of a catalyst composed of rhodium, manganese, lithium and scandium supported on a silica carrier, a catalyst composed of rhodium, molybdenum, iridium, copper and palladium supported on a silica carrier, and a catalyst composed of rhodium, magnesium, zirconium and lithium supported on a silica carrier.

Also provided is the method for producing ethanol, including purifying a raw material gas thermochemically generated from biomass, reacting the raw material gas in an ethanol synthesizer, converting unreacted raw material gas and byproduct gas separated from the reaction product into carbon monoxide and hydrogen by a reforming reaction treatment in a lower hydrocarbon reformer and circulating the carbon monoxide and hydrogen to the ethanol synthesizer, separating a crude ethanol liquid in a multistage distillation column, and converting acetaldehyde, acetic acid and ethyl acetate into ethanol in a hydrogenator provided with a catalyst for reaction with hydrogen.

Effect of the Invention

Because the method for producing ethanol according to the present invention uses a catalyst containing rhodium, at least one transition metal and an additional metal, ethanol can be produced directly from a gas containing carbon monoxide and hydrogen which is obtained by a thermochemical gasification reaction of biomass with high efficiency.

BRIEF DESCRIPTION OF DRAWINGS

FIG. 1 is a view illustrating the procedure from gasification of biomass to production of ethanol.

EMBODIMENT FOR CARRYING OUT THE INVENTION

While the method for producing ethanol and the catalyst for ethanol production according to the present invention is suitable for use with any gas containing carbon monoxide and hydrogen, a method that uses a biomass gas containing carbon monoxide and hydrogen which is obtained by a thermochemical reaction of biomass as a raw material gas is described as an example.

FIG. 1 is a view illustrating the procedure from gasification of biomass by a thermochemical reaction to production of ethanol.

In an ethanol production process 1 of the present invention, biomass and superheated steam supplied from a biomass supply part 2 and a steam supply part 3, respectively, are supplied to a gasification furnace 4 provided with a reforming catalyst to generate a raw material gas containing hydrogen and carbon monoxide at a high temperature.

While various types of gasification furnaces can be used as the gasification furnace 4, a fluidized bed type gasification furnace is preferred. The gasification furnace has supplying means for supplying biomass, heating means for heating the gasification furnace including a reforming catalyst, biomass supplying means for supplying biomass, and means for supplying superheated steam and an oxidant.

Byproduct lower hydrocarbons such as methane and ethane, benzene, poly-condensed ring aromatic hydrocarbons and oil-tar components contained in the biomass gas obtained by a thermochemical reaction of biomass can be also converted into a reformed gas. This improves the conversion efficiency of the gasification of biomass and a biomass gas can be obtained in an amount of 60% or greater based on the biomass. As the biomass gas, a gas primarily composed of carbon monoxide, hydrogen, methane, ethane, ethylene and carbon dioxide can be obtained. In addition, the hydrogen yield can be increased by a highly efficient gasification reaction of byproduct lower hydrocarbons, such as methane, ethane and ethylene, so that a raw material gas having a hydrogen/carbon monoxide ratio of 2 or greater can be supplied for an ethanol synthesis reaction. Therefore, ethanol can be produced with high yield and high selectivity using an ethanol synthesizer coupled to the biomass gasifier.

Examples of the biomass for use in the present invention include plant-derived biomass, such as wood (e.g., Japanese cedar), wooden construction waste, sorghum, sugarcane residue called bagasse, sugar beet residue and rice straws, and industrial waste biomass. Other examples include ground and dried products of a wide variety of unused biomass materials such as dry sludge from water and sewage plants and livestock manure.

The ground biomass product preferably has an average particle size of 5 mm or smaller. A ground biomass product with an average particle size of greater than 5 mm slows the reaction and makes it difficult to achieve high-efficiency gasification. A ground biomass product with an average particle size of smaller than 0.05 mm causes a decrease in grinding efficiency.

By a pyrolysis reaction at 800° C. and steam reforming gasification in the presence of a reforming catalyst, 1 to 2 Nm³ of raw material gas containing 45 to 75% of a synthesis gas composed of 30 to 50% by volume of carbon monoxide hydrogen, 5 to 15% by volume of and methane, 2 to 5% by volume of ethane and 6 to 12% by volume of carbon dioxide can be obtained per kilogram of a dry biomass such as Japanese cedar powder, sorghum or rice straws.

In general, when steam is added to a biomass material to carry out a pyrolysis reaction in the presence of a reforming catalyst, the following reactions occur.

$$CO + H_2O \rightarrow CO_2 + H_2 \quad \text{Formula 1}$$

$$C + H_2O \rightarrow CO + H_2 \quad \text{Formula 2}$$

$$C + 2H_2O \rightarrow CO_2 + 2H_2 \quad \text{Formula 3}$$

$$CH_4 + H_2O \rightarrow CO + 3H_2 \quad \text{Formula 4}$$

$$CH_4 + CO_2 \rightarrow 2CO + 2H_2 \quad \text{Formula 5}$$

In order to synthesize ethanol with high yield and high selectivity from a raw material gas containing a synthesis gas composed of hydrogen and carbon monoxide, the hydrogen/carbon monoxide molar ratio is preferably 2 or greater. For this reason, the reaction conditions should be adjusted so that the reactions represented by Formulae 1 to 5 above can proceed smoothly.

The reaction temperature in the gasification furnace 4 is preferably adjusted to 700 to 1000° C. By controlling the temperature in the gasification furnace including a reforming catalyst in a high temperature range, the hydrogen yield can be increased and a raw material gas having a hydrogen/carbon monoxide molar ratio of 2 or greater can be obtained. The reforming catalyst is preferably adjusted to 400 to 650° C.

A nickel-based catalyst can be used as a reforming catalyst in the gasification furnace 4. Byproduct lower hydrocarbons such as methane and ethane, benzene, poly-condensed ring aromatic hydrocarbon and tar components formed from the biomass can be thereby further reformed into a gas. As a result, the conversion efficiency of the gasification of biomass can be improved and a raw material gas can be obtained in an amount of 60% or greater based on the biomass.

In addition, the hydrogen yield can be increased by an efficient gasification reaction of byproduct lower hydrocarbons such as methane and ethane, and a raw material gas having a hydrogen/carbon monoxide ratio of 2 or greater can be obtained. As a result, bioethanol can be produced in an ethanol synthesizer coupled to the biomass gasifier with high yield and high selectivity.

Ash is discharged from the gasification furnace 4 through an ash outlet port 10, and the generated raw material gas is supplied to a hydrogen reduction reactor 5 to reduce sulfur compounds and nitrogen compounds such as ammonia and amines by reaction with hydrogen supplied from a hydrogen supply part 8. As the hydrogen reduction reactor 5, a device with a cobalt-molybdenum catalyst or the like can be used. The hydrogen supply part 8 can be supplied with hydrogen obtained in a lower hydrocarbon reformer.

Then, desulfurization is carried out in a desulfurizer 6 to remove sulfur compounds such as hydrogen sulfide ($H_2S$), carbonyl sulfide (COS) and carbon disulfide ($CS_2$). As the desulfurizer 6, a desulfurizer using a zinc oxide desulfurizing agent or the like can be used.

A gas-liquid separator 7a coupled to an outlet part of the desulfurizer 6 separates condensed water from the raw material gas purified in the hydrogen reduction reactor 5 and the desulfurizer 6 and discharges the separated condensed water through a condensed water discharge port 9.

The purified raw material gas is pressurized to a pressure in the range of 0.2 to 5.1 MPa, preferably in the range of 1.0 to 3 MPa, and heated to a temperature in the range of 200 to 400° C., preferably in the range of 250 to 300° C., in a compressor 11a. The raw material gas is then brought into contact with an ethanol synthesis catalyst in the ethanol synthesis reactor 12 at a space velocity (SV: raw material gas flow rate L/h/catalyst volume L) of 1000 to 12000 L/h, preferably SV=3000 to 10000 L/h, to cause an ethanol synthesis reaction.

The ethanol synthesis reactor 12 has supplying means for supplying the raw material gas to the ethanol synthesis catalyst and heating means provided around the ethanol synthesis catalyst to heat the ethanol synthesis catalyst, and a gas-liquid separator 7b coupled to an outlet part of the ethanol synthesis catalyst separates and recovers a liquid product having, for example, a 50 to 60 volume percent concentration ethanol from the outlet reaction gas containing unreacted raw material gas and byproduct methane and ethane.

The outlet gas separated in the gas-liquid separator 7b and containing unreacted raw material gas and byproduct methane and ethane is circulated under pressure, or circulated under pressure after the lower hydrocarbons such as methane and ethane in the outlet gas are subjected to a reforming reaction treatment using a nickel-ruthenium catalyst in a lower hydrocarbon reformer 15 to convert them into a synthesis gas ($H_2$, CO), by a circulation compressor 11b through the ethanol synthesis reactor 12 to cyclically repeat the reaction three to five times. At the same time, off gas is discharged through an off gas outlet port 14.

As a result, in the process of synthesizing ethanol from the raw material gas, the conversion yield and selectivity of ethanol from the raw material gas based on carbon monoxide can be increased, and the yield of ethanol that can be produced from 1 ton of unit biomass can be increased to 0.3 to 0.5 tons.

The liquid product separated in the gas-liquid separator 7b is supplied to a multistage distillation column 16. The gas-liquid separator 7b is provided with a liquid product outlet port 13.

The liquid product is concentrated in the multistage distillation column 16 to an ethanol concentration of 79 to 90% by volume, and low-boiling point residues, such as acetic acid, acetaldehyde, propanol and methanol, are separated and recovered in recovery means 17. As the multistage distillation column 16, a distillation column with Raschig rings can be used.

The crude ethanol liquid obtained in the multistage distillation column 16 is fed by a liquid supply pump 18 to a hydrogenation reactor 19 with a catalyst for reaction with hydrogen, where acetic acid, acetaldehyde, ethyl acetate and so on remaining in the crude ethanol liquid are converted into ethanol to increase the yield. Examples of the catalyst for reaction with hydrogen include CuZnO catalysts and PdFe catalysts.

A hydrogenation reactor can utilize the hydrogen generated in the lower hydrocarbon reformer.

The ethanol after the hydrogenation treatment is brought into contact with an aqueous sodium hydroxide solution supplied through an aqueous sodium hydroxide solution supply port 20 to remove acidic substances and is then subjected to gas-liquid separation in a gas-liquid separator 7c. Then, the ethanol is supplied to a multistage distillation column 21 and 95% by volume ethanol is recovered through an ethanol outlet port 23. The remaining components after the recovery of ethanol are discharged through a remaining component outlet port 25.

In addition, water is removed in a zeolite adsorption separation column 22, and 99 volume percent ethanol is recovered through an ethanol outlet port 24.

In a practical test using an ethanol synthesis reactor with a rhodium catalyst according to the present invention, the ethanol synthesis reactivity is improved by approximately 2 to 10% for a gas material containing a gas mixture of carbon monoxide and hydrogen and additionally containing 10% by volume of methane, ethane, ethylene or carbon dioxide, respectively compared to a gas material free from these additional substances, and the stability of catalytic performance is also improved.

EXAMPLE

Example 1

Preparation of Catalyst 1

A catalyst 1 composed of rhodium, manganese, lithium and scandium supported on a silica carrier was prepared by impregnating a silica carrier (surface area: 185 m$^2$/g) with an aqueous ethanol solution containing chlorides of rhodium, manganese, lithium and scandium such that the atomic ratio of the metals was 1:0.05:0.3:0.15, and subsequently subjecting the silica carrier to an activation treatment in a stream of a gas mixture of hydrogen and nitrogen (volume ratio 1:4) involving heating to 100° C. over one hour followed by maintaining at the temperature for two hours, heating to 400° C. over two hours followed by maintaining at the temperature for two hours, and cooling to 25° C.

Preparation of Cu/ZnO Catalyst 1

A Cu/ZnO catalyst 1 composed of copper and zinc oxide (ZnO) supported on a silica carrier was prepared by impregnating a silica carrier (surface area: 265 m$^2$/g) with an aqueous ethanol solution containing nitrates of copper and zinc such that the atomic ratio of the metals was 1:0.8, and subsequently subjecting the silica carrier to an activation treatment in a stream of a gas mixture of hydrogen and nitrogen (volume ratio 1:2) involving heating to 100° C. over one hour followed by maintaining at the temperature for two hours, heating to 400° C. over two hours followed by maintaining at the temperature for two hours, and cooling to 25° C.

Preparation of Raw Material Gas

A Japanese cedar powder was supplied to an apparatus shown in FIG. 1 at a rate of 10 kg per hour at 800° C. with steam being supplied thereto to produce a raw material gas with a hydrogen/carbon monoxide (volume ratio)=2 at a rate of 15 Nm$^3$ per hour in the gasification furnace.

The obtained raw material gas had a volume composition of 26% carbon monoxide, 54% hydrogen, 10% methane, 1% ethane and 5% carbon dioxide with the balance being nitrogen. The raw material gas was hydrogenated with a CoMo catalyst and purified in a desulfurizer using zinc oxide.

Ethanol Synthetic Test

After being passed through a reactor A filled with the catalyst 1 at 2.5 MPa and a temperature of 280° C., the raw material gas was subjected to a catalytic reaction cyclically in a reactor B directly connected to the reactor A and filled with the Cu/ZnO supporting silica catalyst 1 at 2.5 MPa and a temperature 280° C., whereby ethanol was produced with an ethanol selectivity of 80% (based on carbon monoxide) and an ethanol space time yield of 320 g/catalyst L/h.

Even after 1000 hour reaction, the ethanol synthetic performance was maintained. Water was removed from the ethanol (52% ethanol+39% water (volume ratio)) recovered in the gas-liquid separator by distillation and zeolite adsorption purification treatment, whereby 3.5 kg of 99 volume percent ethanol was obtained.

Example 2

Preparation of Catalyst 2

A catalyst 2 composed of rhodium, molybdenum, iridium, copper and palladium on a silica carrier was prepared by impregnating a silica carrier (surface area: 215 m$^2$/g) with an aqueous ethanol solution containing chlorides of rhodium, molybdenum iridium and palladium and copper nitrate such that the ratio of the metals Rh, Mo, Ir, Cu and Pd was 1:0.3:0.2:0.5:0.3, and subsequently subjecting the silica carrier to an activation treatment in a stream of a gas mixture of hydrogen and nitrogen (volume ratio 1:3) involving heating to 150° C. over one hour followed by maintaining at the temperature for two hours, heating to 450° C. over two hours followed by maintaining at the temperature for two hours, and cooling to room temperature.

Preparation of Raw Material Gas

A raw material gas was produced in the same manner as in Example 1 except that rice straws were used at a rate of 5 kg per hour as the biomass. The raw material gas had a volume composition of 28% carbon monoxide, 48% hydrogen, 3% methane, 1% ethane and 15% carbon dioxide with the balance being nitrogen.

Ethanol Synthetic Test

The purified raw material gas was supplied to a reactor filled with a mixture containing the catalyst 2 and ceramic balls as a diluents material at a volume ratio of 4:1 at 2.5 MPa and a temperature of 280° C.

The reaction gas was subjected to a catalytic reaction at 7.1 MPa, 300° C. and SV=9000 L/h, whereby 250 g catalyst L/h of ethanol and 480 g/catalyst L/h of methanol were obtained with a carbon monoxide conversion rate of 58%.

Example 3

Preparation of Catalyst 3

A catalyst 3 composed of rhodium, zirconium, lithium and magnesium supported on a silica carrier was prepared by impregnating a silica carrier (surface area: 215 m²/g) with an aqueous ethanol solution containing chlorides of rhodium, zirconium, lithium and magnesium such that the atomic ratio of the metals was 1:0.3:0.5:0.8, and subsequently subjecting the silica carrier to an activation treatment in a stream of a gas mixture of hydrogen and nitrogen (volume ratio 1:4) involving heating to 100° C. over one hour followed by maintaining at the temperature for two hours, heating to 400° C. over two hours followed by maintaining at the temperature for two hours, and cooling to room temperature.

Preparation of CuZnTi Catalyst

A CuZnTi catalyst composed of copper, zinc and titanium supported on a silica carrier was prepared by impregnating a silica carrier (surface area: 165 m²/g) with an aqueous ethanol solution containing copper nitrate, zinc nitrate and titanium (III) chloride such that the atomic ratio of the metals copper, zinc and titanium was 1:0.8:0.2, and subsequently subjecting the silica carrier to an activation treatment in a stream of a gas mixture of hydrogen and nitrogen (volume ratio 1:2) involving heating to 100° C. over one hour followed by maintaining at the temperature for two hours, heating to 450° C. over two hours followed by maintaining at the temperature for two hours, and cooling to room temperature.

Preparation of Raw Material Gas

A raw material gas with a hydrogen/carbon monoxide molar ratio=1.5 was produced at a rate of 10 Nm³/h in the same manner as in Example 1 using Japanese cedar pellets at a rate of 10 kg per hour.

Ethanol Synthetic Test

The produced raw material gas was subjected to a catalytic reaction in a device filled with the catalyst 3 and the CuZnTi catalyst at 7.1 MPa, 290° C. and SV=6000 L/h, whereby an ethanol space time yield of 460 kg/catalyst L/h and an acetic acid space time yield of 290 g/catalyst h were obtained.

Comparative Example

Preparation of Catalyst 4

A catalyst 4 composed of iridium, copper and palladium supported on a silica carrier was prepared by impregnating a silica carrier (surface area: 245 m²/g) with an aqueous ethanol solution containing chlorides of iridium and palladium and copper nitrate such that the atomic ratio of the metals iridium, copper and palladium was 1:0.5:0.5, and subsequently subjecting the silica carrier to an activation treatment in a stream of a gas mixture of hydrogen and nitrogen (volume ratio 1:2) involving heating to 100° C. over one hour followed by maintaining at the temperature for two hours, heating to 350° C. over two hours followed by maintaining at the temperature for two hours, and cooling to room temperature.

Ethanol Synthetic Test

When an ethanol synthetic test was conducted in the same manner as in Example 1 except that the raw material gas used in Example 1 was reacted in a reactor filled with the catalyst 4 at 2.5 MPa and 280° C., ethanol was 0.5 to 1 g/catalyst L/h and the ethanol selectivity based on carbon monoxide was 1% or lower after 100 hours.

INDUSTRIAL APPLICABILITY

The method for producing ethanol and the catalyst for use in the production of ethanol according to the present invention allows high-yield production of ethanol from a raw material gas obtained by a thermochemical gasification reaction of biomass. Therefore, ethanol can be produced from less fermentable biomass materials such as plant-derived materials and rice straws and industrial waste biomass materials such as wooden building materials and pulp. As a result, an economical ethanol synthesis method which can broaden the range of raw materials is provided.

DESCRIPTION OF REFERENCE NUMERALS

1: ethanol production process
1: biomass supply part
2: steam supply part
3: gasification furnace
4: reduction reactor
5: desulfurizer
7a: gas-liquid separator
7b: gas-liquid separator
7c: gas-liquid separator
8: hydrogen supply part
9: condensed water discharge port
10: ash outlet port
11a: circulation compressor
11b: circulation compressor
12: ethanol synthesis reactor
13: liquid product outlet port
14: off gas outlet port
15: lower hydrocarbon reformer
16: multistage distillation column
17: recovery means
18: liquid supply pump
19: hydrogenation reactor
20: aqueous sodium hydroxide solution supply port
21: multistage distillation column
22: zeolite adsorption separation column
23: ethanol outlet port
24: ethanol outlet port
25: remaining component outlet port

The invention claimed is:

1. A method for producing ethanol, comprising a step of synthesizing ethanol by reacting a raw material gas in the presence of a catalyst,
  wherein the raw material gas is biomass gas primarily containing hydrogen, carbon monoxide, carbon dioxide, and a low hydrocarbon, obtained by a thermochemical gasification reaction of biomass, and
  wherein the step of synthesizing ethanol is conducted in the presence of an ethanol synthesis catalyst (1) or (2):
  (1) a catalyst comprising rhodium, manganese, lithium, and scandium supported on a silica carrier, or
  (2) a catalyst comprising rhodium, magnesium, zirconium, and lithium supported on a silica carrier;
  wherein ethanol is synthesized with a higher selectivity than acetic acid and acetaldehyde which are the same C2-oxygenates as the ethanol.

2. The method for producing ethanol according to claim 1, characterized by purifying a raw material gas thermochemically generated from biomass, reacting the raw material gas in an ethanol synthesis reactor, converting unreacted raw material gas and byproduct gas separated from the reaction product into carbon monoxide and hydrogen by a reforming reaction treatment in a lower hydrocarbon reformer and then circulating the reformed gas containing carbon monoxide and hydrogen to the ethanol synthesis reactor, separating a crude ethanol liquid in a multistage distillation column, and converting acetaldehyde, acetic acid and ethyl acetate into ethanol in a hydrogenation reactor provided with a catalyst for reaction with hydrogen.

3. The method for producing ethanol according to claim 1, wherein 10% to 19% by volume of the biomass gas consists of a mixture of carbon dioxide and low hydrocarbons.

4. The method for producing ethanol according to claim 1, wherein the low hydrocarbon is selected from the group consisting of methane, ethane and ethylene.

\* \* \* \* \*